US012279848B1

(12) United States Patent
Hale (10) Patent No.: US 12,279,848 B1
(45) Date of Patent: Apr. 22, 2025

(54) DISPOSABLE MEDICAL DRAPE

(71) Applicant: Protection Products, Inc., Hickory, NC (US)

(72) Inventor: Jeffrey Wayne Hale, Hickory, NC (US)

(73) Assignee: Protection Products, Inc., Hickory, NC (US)

( * ) Notice: Subject to any disclaimer, the term of this patent is extended or adjusted under 35 U.S.C. 154(b) by 1017 days.

(21) Appl. No.: 17/173,808

(22) Filed: Feb. 11, 2021

Related U.S. Application Data

(60) Division of application No. 16/026,245, filed on Jul. 3, 2018, now Pat. No. 11,065,073, which is a continuation-in-part of application No. 15/380,149, filed on Dec. 15, 2016, now Pat. No. 10,820,956.

(60) Provisional application No. 62/267,673, filed on Dec. 15, 2015.

(51) Int. Cl.
*A61B 46/00* (2016.01)
*A61B 50/10* (2016.01)
*A61G 13/10* (2006.01)

(52) U.S. Cl.
CPC ........... *A61B 46/40* (2016.02); *A61B 50/10* (2016.02); *A61G 13/102* (2013.01)

(58) Field of Classification Search
CPC ......... A61B 46/10; A61B 46/20; A61B 46/27; A61B 46/30; A61B 46/40; A61B 2046/201; A61B 50/10; A61B 50/15; A61B 2050/155; A61G 13/121; A61G 13/1235; A61G 13/124; A61G 13/1245; A61G 13/125; A61F 15/004
See application file for complete search history.

(56) References Cited

U.S. PATENT DOCUMENTS

| | | | | |
|---|---|---|---|---|
| 3,335,719 A | * | 8/1967 | Boucher | A61B 46/00 206/440 |
| 3,424,153 A | * | 1/1969 | Lewis, Jr. | A61F 13/06 2/242 |
| 3,494,356 A | * | 2/1970 | Melges | A61B 46/30 128/849 |
| 3,650,267 A | | 3/1972 | Anderson | |
| 3,667,458 A | | 6/1972 | Krebs | |
| 4,349,019 A | * | 9/1982 | Singer | A61B 46/30 128/856 |
| 4,883,695 A | * | 11/1989 | Weimar | A61G 13/10 428/36.1 |
| 4,923,453 A | | 5/1990 | Bullard, Jr. | |
| 5,156,167 A | | 10/1992 | Busch | |
| 5,170,804 A | | 12/1992 | Glassman | |

(Continued)

FOREIGN PATENT DOCUMENTS

CN 204468305 7/2015

*Primary Examiner* — Keri J Nelson
(74) *Attorney, Agent, or Firm* — MacCord Mason PLLC (57) ABSTRACT

Drape systems, apparatuses and methods are provided. In some aspects a drape may create an impervious barrier for preventing medical contaminants from contaminating a medical table and/or a medical table base. One drape embodiment includes a central portion, a first end cover and a second end cover, and first and second side portions having fold portions for forming troughs. A drape embodiment may include an absorbent surface having a discontinuous section and in inner perimeter for forming a barrier about a medical table base.

9 Claims, 13 Drawing Sheets

(56) References Cited

U.S. PATENT DOCUMENTS

| | | | | |
|---|---|---|---|---|
| 5,342,286 | A | * | 8/1994 | Kelly ................ A61F 15/004 |
| | | | | 602/62 |
| 5,640,975 | A | | 6/1997 | Diao |
| 5,704,370 | A | * | 1/1998 | Gawarecki ............ A61G 13/10 |
| | | | | 128/849 |
| 5,713,372 | A | | 2/1998 | Pinney et al. |
| 5,845,641 | A | | 12/1998 | Pinney et al. |
| 6,126,621 | A | * | 10/2000 | Aceves ................ A61F 13/041 |
| | | | | 128/878 |
| 6,436,085 | B1 | | 8/2002 | Lauer |
| 6,824,853 | B1 | * | 11/2004 | Levine ................ A61B 46/40 |
| | | | | 405/60 |
| 7,905,847 | B2 | * | 3/2011 | Barker ................ A61F 15/008 |
| | | | | 602/62 |
| 8,206,363 | B2 | * | 6/2012 | Bainbridge ............ A61B 46/27 |
| | | | | 604/293 |
| 2010/0275929 | A1 | | 11/2010 | Kaska |
| 2013/0112212 | A1 | | 5/2013 | Schwertner |
| 2018/0160980 | A1 | * | 6/2018 | Balderama Arenas ...................... |
| | | | | A61B 5/702 |

* cited by examiner

DISPOSABLE MEDICAL DRAPE

This application is a divisional of U.S. application Ser. No. 16/026,245, filed Jul. 3, 2018, which is a continuation in part of U.S. application Ser. No. 15/380,149, filed Dec. 15, 2016, now U.S. Pat. No. 10,820,956, issued Nov. 3, 2020, which claims the benefit of U.S. provisional application No. 62/267,673, filed Dec. 15, 2015, which is herein incorporated by reference.

FIELD OF THE TECHNOLOGY

The invention of the present disclosure relates generally to disposable medical drapes and, more particularly, to systems, apparatus and methods for draping medical tables, equipment and personnel in medical situations, for example, in hospitals, emergency room and surgical procedures.

BACKGROUND

Advances in medical science have brought technological improvement and more sophisticated equipment into the medical setting. By way of example, many medical tables in use today in operating and emergency rooms are highly mechanized and adaptable to many different needs and scenarios. As compared to more simple conventional medical tables, medical tables today are often specialized, computerized and fully adjustable. The table controls and computerized parts may actually reside within the table itself, for example, at or in the base of the table. These tables are quite expensive, and while solving many medical needs, challenges have arisen to prevent contamination of such equipment which must then be taken out of use for extensive, time consuming and meticulous decontamination. Even worse, contamination and fluids reaching the computerized table parts could indefinitely or permanently take a medical table out of service.

Preventing exposure of personnel has long been a concern in the medical field, particularly in surgical and emergency room procedures where blood, body fluids, medications and irrigation fluids can quickly accumulate to produce large amounts of fluids that are released. During intense medical treatment, for example in high trauma situations, the doctors and medical staff should be able to focus on the patient and not be expected to turn their focus to clean-up and control of the possibly contaminating fluids during the patient's treatment. In certain injuries, such as injuries to the head, chest and abdomen, higher than average amounts of blood and irrigation fluids may be discharged, compounding the contamination and fluid control problem. Issues with health, contamination, cross-contamination and safety are of major concern, especially in these types of situations. These concerns are also balanced with the economics involved with providing a solution, as many alternatives are cost prohibitive in hospital and first responder scenarios.

Applicant realizes that not only is contamination of personnel an issue of concern but also contamination and/or exposure of equipment, for example, the more advanced, computerized equipment and medical tables. In the past, standard medical tables were more manual, simple and easier to clean, however, rapidly developing advancements in such equipment now creates much larger contamination concerns. The computerized tables have sensitive electronics that complicate the decontamination process. Today, hospital reimbursement rates may be affected by contamination mitigation and patient health depends on sterile environments, and expensive computerized table contamination can cause cross-contamination exposure and, thus, increasing costs and health threats. Applicant believes improvement is needed toward these and other challenges.

Therefore Applicant desires an economical drape system, apparatuses and methods that provide better management of fluids in medical situations to minimize contamination and safety concerns.

SUMMARY

In accordance with the present disclosure, drapes, drape systems and methods are provided for containing waste fluids and the like. This disclosure provides improved drapes, kits, assemblies and methods that are convenient, efficient, and safe for the user.

A drape for containment of medical waste fluids may include a central portion, a first side portion having a first fold portion, a second side portion having a first fold portion, a first end cover, and a second end cover. There may be at least one attachment point on the first side portion and/or at least one attachment point on the second side portion. The first fold portion may be configured to double over the first side portion along a fold to form a trough. Another first fold portion may be configured to double over the second side portion along a fold to form a trough.

The drape may include sealed seams to form an impervious barrier at least about the top and sides of the medical table.

In other embodiments, a table base drape may include a top surface, a bottom surface, a first end, and a second end. The table base drape may be configured to form a perimeter around a table base. An opening may be included in the table base drape for fitting the drape around a table base.

Some embodiments include at least one drape cover extension including a flap for covering a gap in the space between the drape and the drape cover extension, the flap extending between the drape and a drape cover extension body.

A drape system may include a drape and a table base drape. In some examples the drape and table base drape may be one-use and disposable.

Methods for a drape system are also included. One example includes a method for protecting a medical table and/or a medical table base by any of the drapes disclosed. Some examples include methods for containment of medical waste fluids by any of the drapes disclosed.

These and other aspects of the inventions of the present disclosure will become apparent to those skilled in the art after a reading of the following description of the preferred embodiment when considered with the drawings.

The above summary was intended to summarize certain embodiments of the present disclosure. Embodiments will be set forth in more detail in the figures and description of embodiments below. It will be apparent, however, that the description of embodiments is not intended to limit the present inventions, the scope of which should be properly determined by the appended claims.

BRIEF DESCRIPTION OF THE DRAWINGS

Embodiments of the disclosure will be better understood by a reading of the Description of Embodiments along with a review of the drawings, in which.

DESCRIPTION OF EMBODIMENTS

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms.

Figure 1:
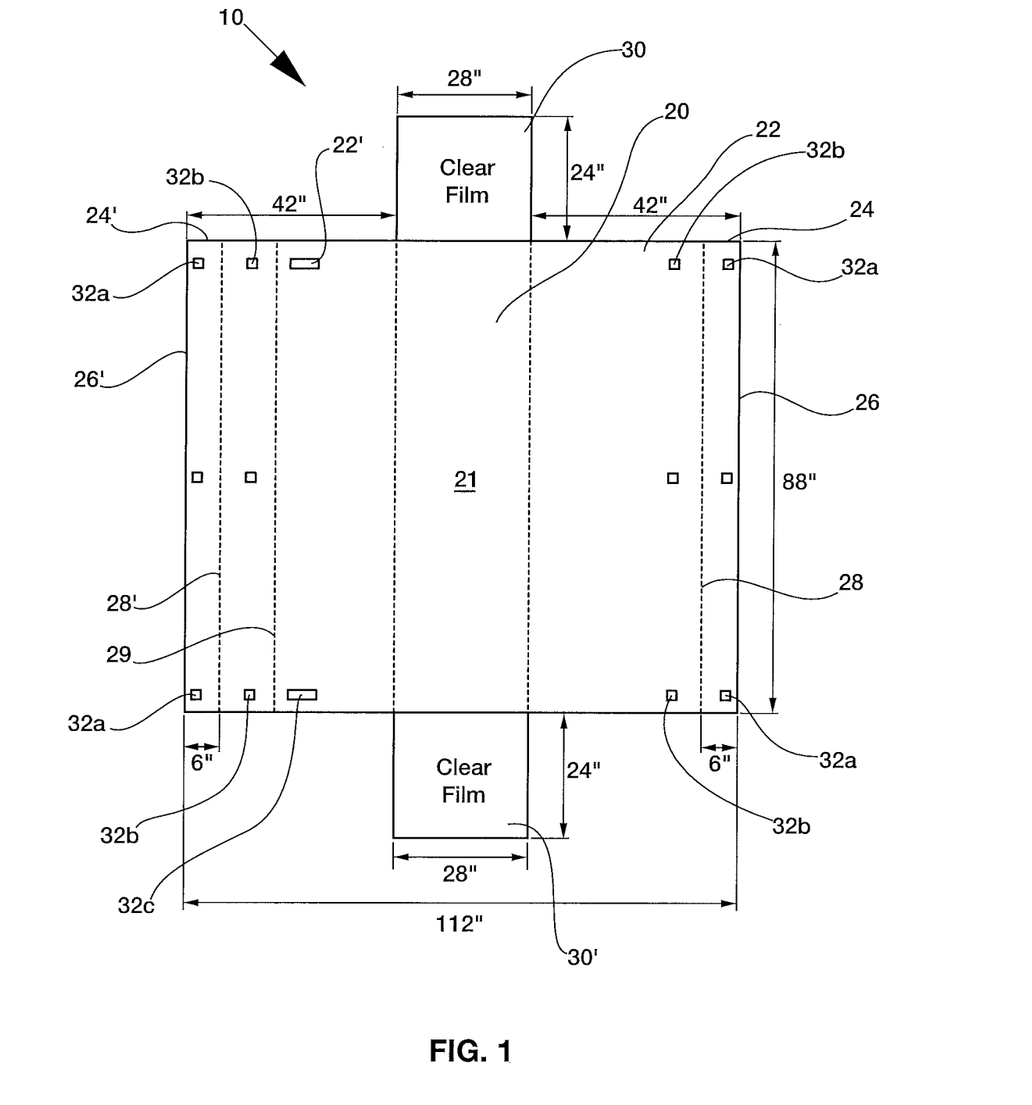
FIG. 1 is a top planar view of one example of a drape according to the present disclosure.

Referring now to the drawings in general and FIG. 1 in particular, it will be understood that the illustrations are for the purpose of describing embodiments of the disclosure and are not intended to limit the disclosure or any invention thereto.

Figure 1A:
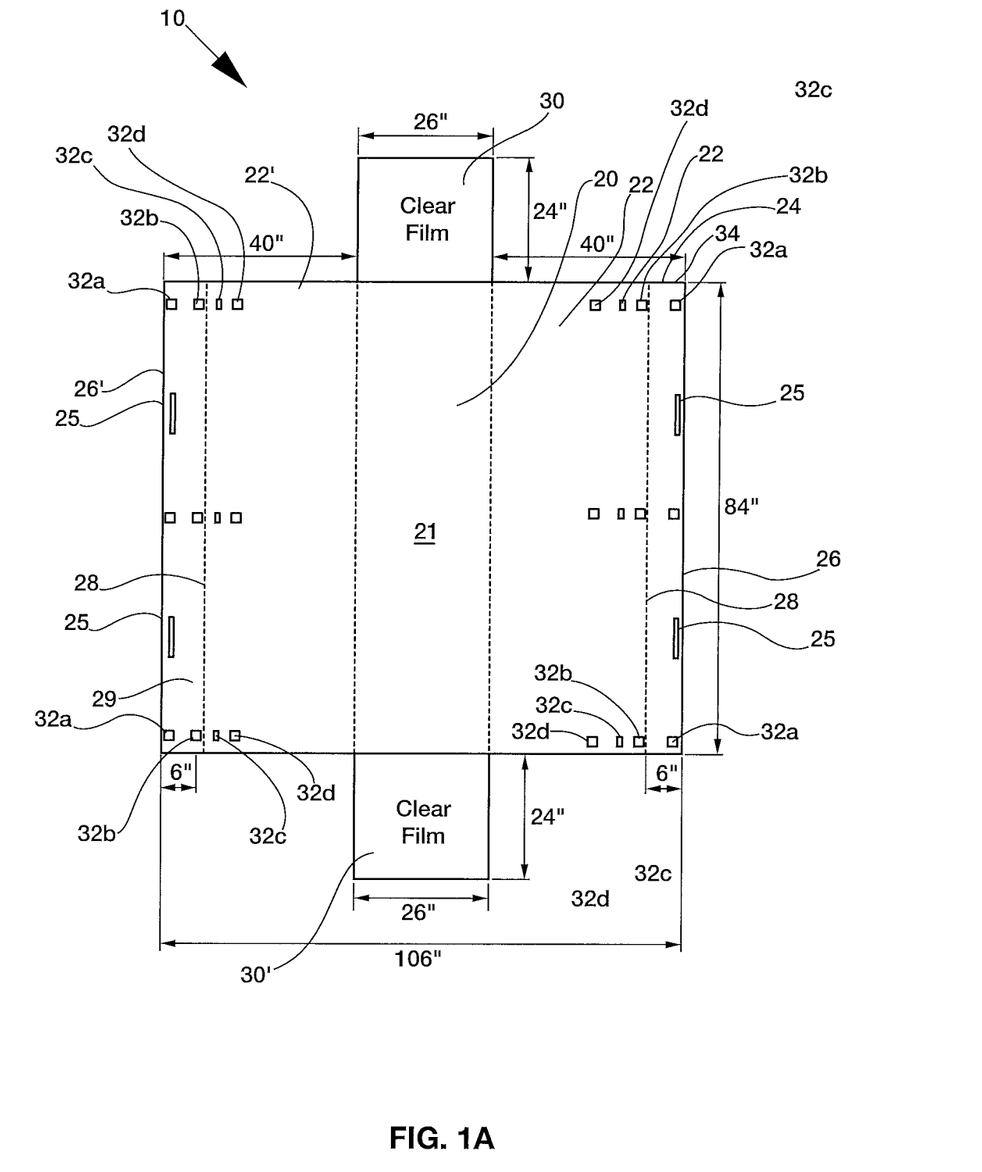
FIG. 1A is a top planar view of another example of a drape according to the present disclosure.

FIGS. 1-1A shows a top view of examples of a drape, generally designated 10, according to the present disclosure. The drape 10, for containment of medical waste fluids, may include in some embodiments, a top surface 21 and a bottom surface 23, a central portion 20, a first side portion 22 and a second side portion 22'. The first side portion 22 may include at least a first fold portion 24. The second side portion 22' may include at least a first fold portion 24, a second fold portion 24', etc. Any number of fold portions may be accommodated. The first side portion may also include one or more attachment points 32a, 32b. The second side portion may include one or more attachment points 32a, 32b. The first side portion 22 and second side portion 22' may often have secondary attachment points 32c. The attachment points 32a, 32b, 32c and 32d may be spaced apart horizontally along the length of the side portions and extend vertically upward from a distal edge of the side portions 26, 26'. Any number of attachment points is considered within the scope of this disclosure.

The first and/or second side portions 26, 26' may be extended lengths. Some embodiments include an extended length that drapes over the side of the table and extends downward at least half way between the table and the floor. In some examples, the extended length may drape over the side of the table downward and extend at least ¾ way between the table and the floor. In some examples, the extended lengths may be between about 34" to about 50". An extended length provides more cover for the table and table area and helps prevent medical waste fluid escaping the central portion from running over the edges of a top of the table and spilling onto the floor and/or under the table and onto what may be the mechanized table parts, often found in the base of the table.

Figure 2:
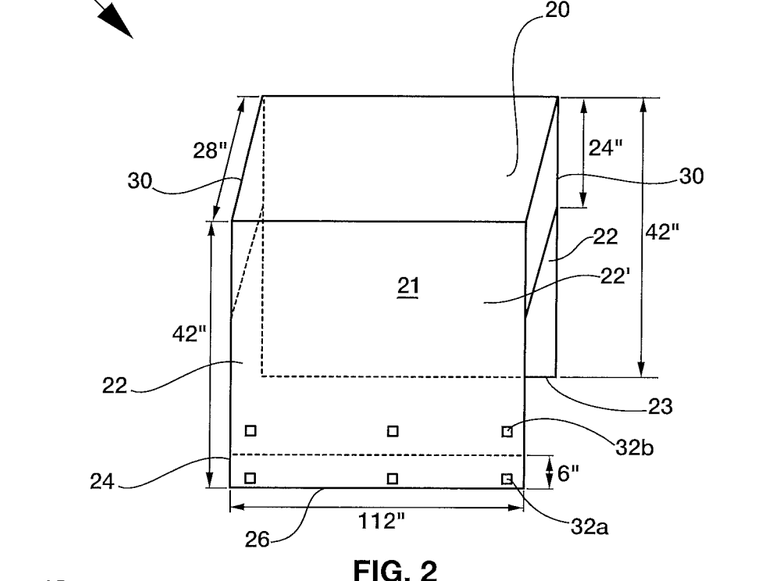
FIG. 2 is a side perspective view of one example of a drape folded according to the present disclosure.
Figure 3:
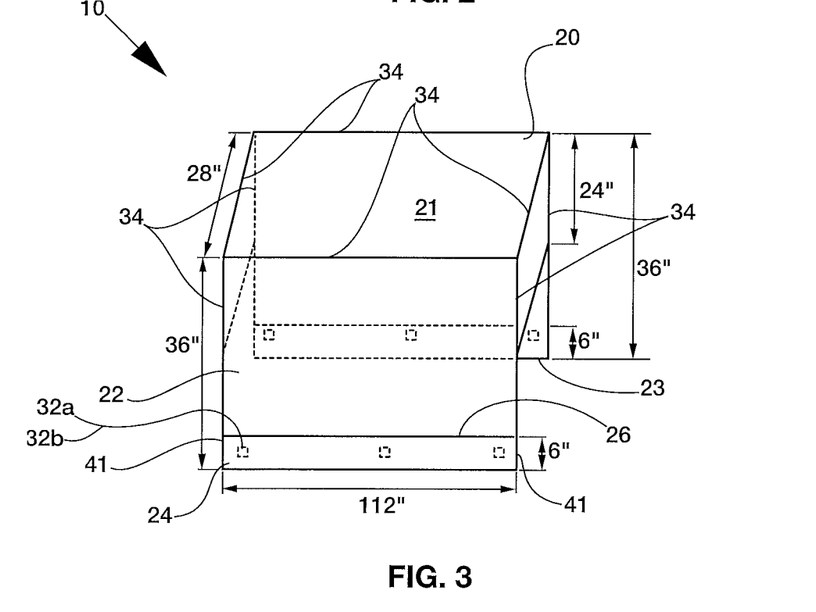
FIG. 3 is a perspective side view of another example of a drape according to the present disclosure.
Figure 3A:
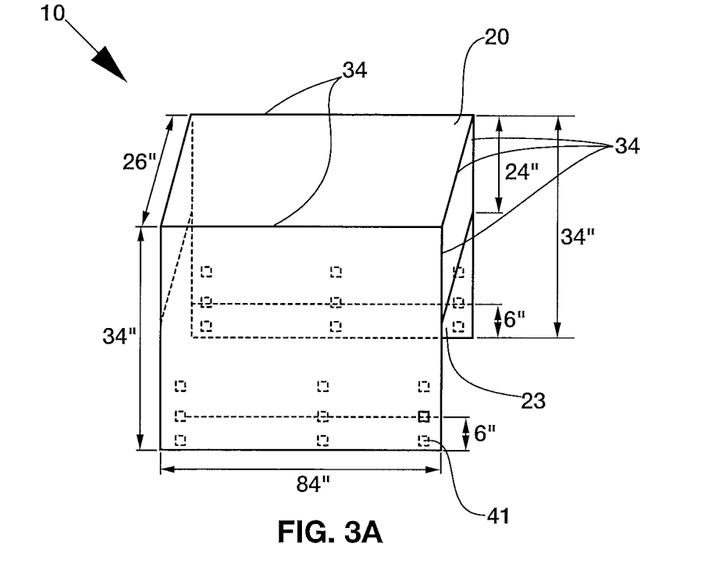
FIG. 3A is a perspective side view of another example of a drape according to the present disclosure.

The fold portion 24, 24' may be of varying lengths and configured to be turned upward by a distal edge 26, 26' so that the fold portions are doubled over at a fold 28 such that the side portions form a trough 41, as seen in FIGS. 2 and 3A. A trough 41 may be formed on the first side and/or on the second side. The fold portions may be secured at attachment points 32. The fold portion may include at least one attachment point 32a. The attachment point 32a may mate with an attachment point on the side portion 22, 22'. The attachment point on the side portion 22, 22' may be spaced apart from an upper edge of the side portion 22, 22', where the side portion attaches to the central portion 20, so that the trough 41 is not in contact with central portion 20. The trough 41 may be formed on a lower part of the side portion 22, 22' so that the trough 41 and collection and absorption of waste fluids by the trough 41 are kept away from a table work space and away from the table top and table top edges where medical personnel may be working in close proximity to the patient and the table. In some cases, where fluids are puddled/pooled in a fluid collection reservoir too near the table top, the reservoir may get in the way of medical personnel or may be placed under pressure as workers lean over the table, forcing some fluids to escape a collection point in conventional table covers.

The trough 41 size may be variable. The trough 41 may be continuous at the bottom of the trough. The trough 41 may be open on at least one side at the top of the trough 41. The trough may be open along the ends of the trough 41. When a trough 41 is formed, waste fluids escaping beyond the central portion 20 may be encouraged to flow along the side portions 22, 22' and/or gather in the trough 41 to be absorbed by the drape. The trough helps prevent excess medical waste fluids from spilling over the medical table and onto the floor and/or onto medical personnel. Collection of the medical wastes in the trough 41 assists in easier and more sanitary cleanup post procedure and prevents spillage of fluids over the side of the table and onto the lower table.

Trough 41 may be an adjustable height trough, and in other embodiments may include fixed height cuffs with predetermined trough size. By way of example, adjustable height troughs may be beneficial in situations where the height of the table and/or the height of the doctor is unpredictable and often changing, for example in trauma surgery. In other scenarios, fixed height cuff troughs 41 may be useful in situations such as emergency surgeries with less variability, for example, C-sections surgeries.

The drape 10 may also include a first end cover 30 and/or a second end cover 30'. The end cover 30, 30' may be, in some examples a clear film. End cover 30, 30', as seen in FIGS. 2-3A, may be interfaced with the central portion 20 and at least a part of side portions 22, 22' to from a complete cover for a medical table, covering past the top, ends and sides of a medical table. In some examples, the interface between the end cover 30, 30' with the central portion 20 and side portions 22, 22' may be sewn and/or sealed to create an integrally formed one-piece drape 10 cover for a medical table that encloses the top and sides of the medical table forming a barrier preventing contamination from reaching the table. In some examples, a heat seal or double adhesive may connect the end cover 30, 30' to the central portion 20 and/or the side portions 22, 22' to ensure no fluid pathways remain at the interface points of the drape. In some examples, the seams included in the drape 10 are sealed seams to form an impervious fitted drape.

The drape 10 may include more than one trough 41 forming a trough system. The trough system allows for comprehensive protection, for example, of mechanized tables, as well as for the adjustment of the size of the drape to accommodate both variation to surgeon height and alternate patient positioning (head down, head up, side tilt, etc.).

In other examples, the invention may be considered a drape 10 having adjustable collection troughs that are not fixed in dimension and that are extended downward from the table sides toward the floor. In other embodiments, drape 10 may be considered an impermeable drape for covering the entire surface of a medical table and forming a barrier between medical wastes and the medical table. The drape, in this embodiment, includes extended sides having troughs, the drape encapsulating the medical table to prevent fluid migration to internal table surfaces by absorbing and containing fluid by way of absorbent areas. The superabsorbent material may be dispersed throughout the drape and/or may be in sections on the top, along the sides and in the trough of the drape. In some examples, the ends of the trough 41 may be open and not bound.

Figure 2A:
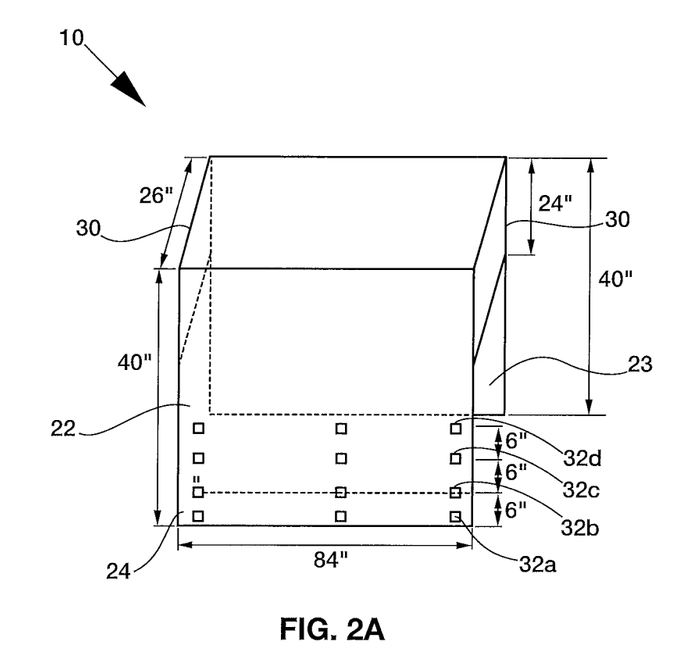
FIG. 2A is a perspective side view of one example of a drape according to the present disclosure.

FIGS. 2 and 2A shows an adjustable trough 41. FIGS. 3 and 3A show a portion of the side portion 22, 22' upturned and to form a trough 41 and secured at attachment points 32.

Drape 10 may include malleable strips 25 along the edge of the trough 41 to shape the turned up edge of the trough to insure fluid does not roll over the outside edge of the turned up section of the drape. By way of example, any malleable material able to hold its shape will work for the malleable strips 25. For example, the strips may be malleable aluminum strips.

Figure 4:
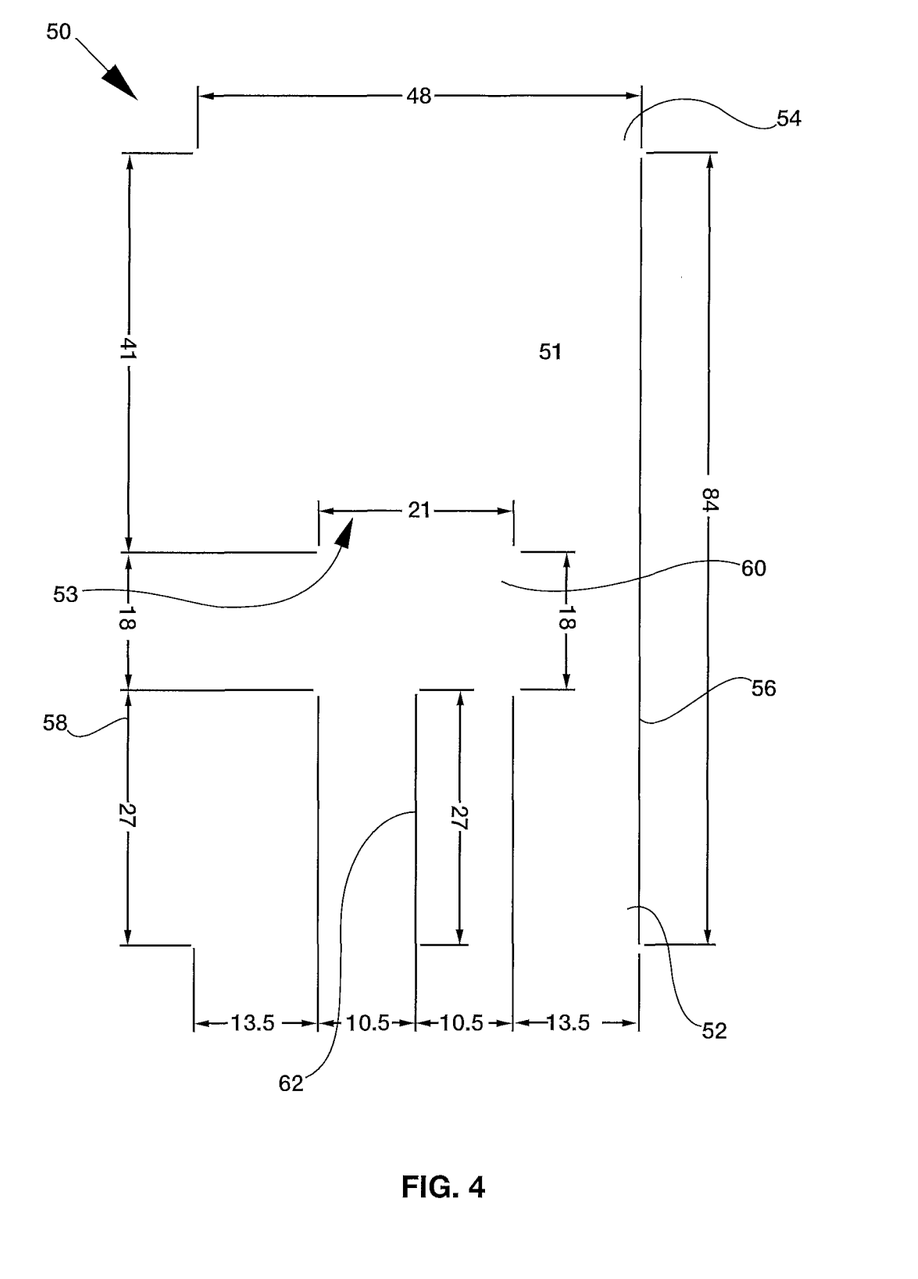
FIG. 4 is a top planar view of a table base drape according to the present disclosure.
Figure 5:
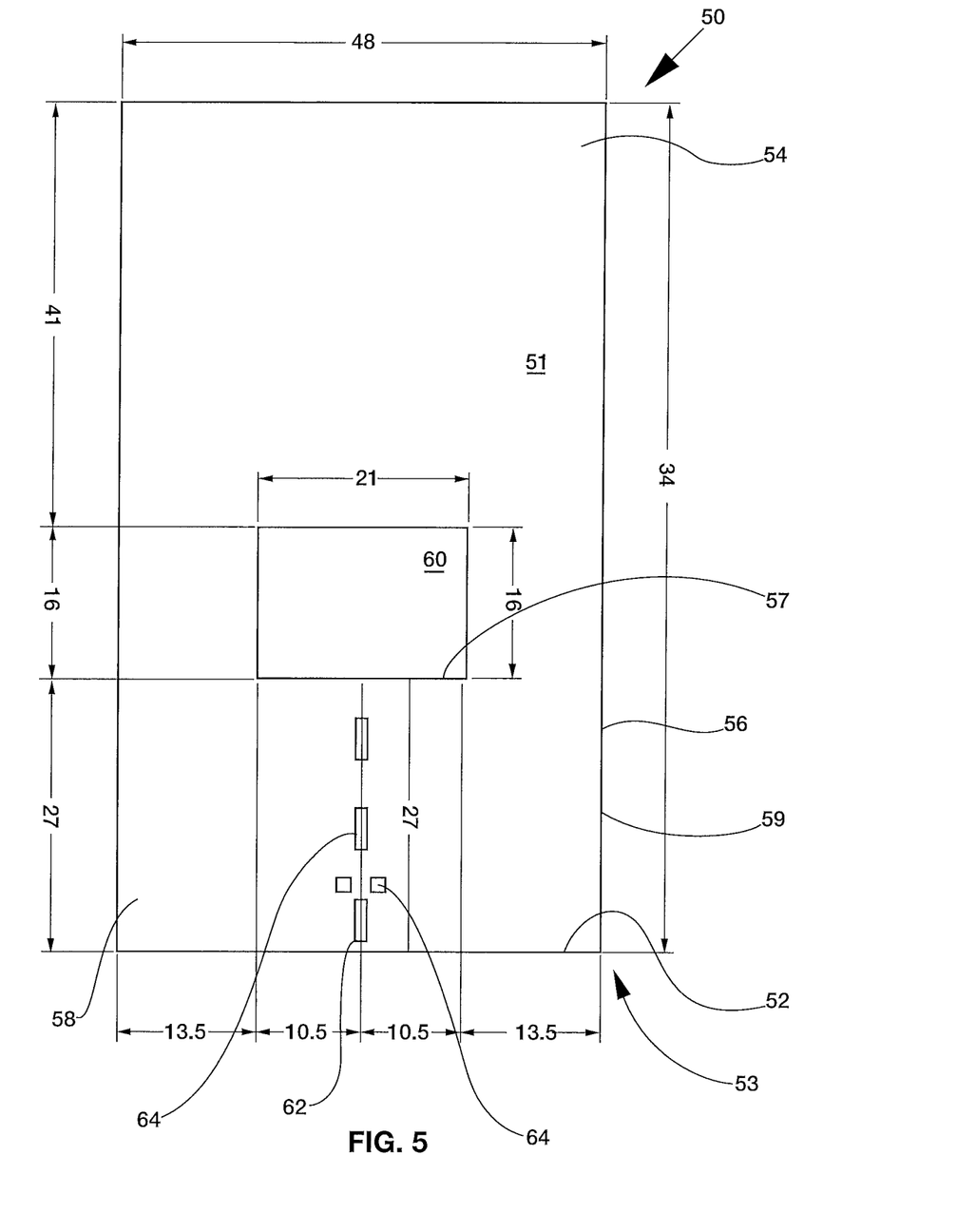
FIG. 5 is another top planar view of another example of a table base drape according to the present disclosure.
Figure 6:
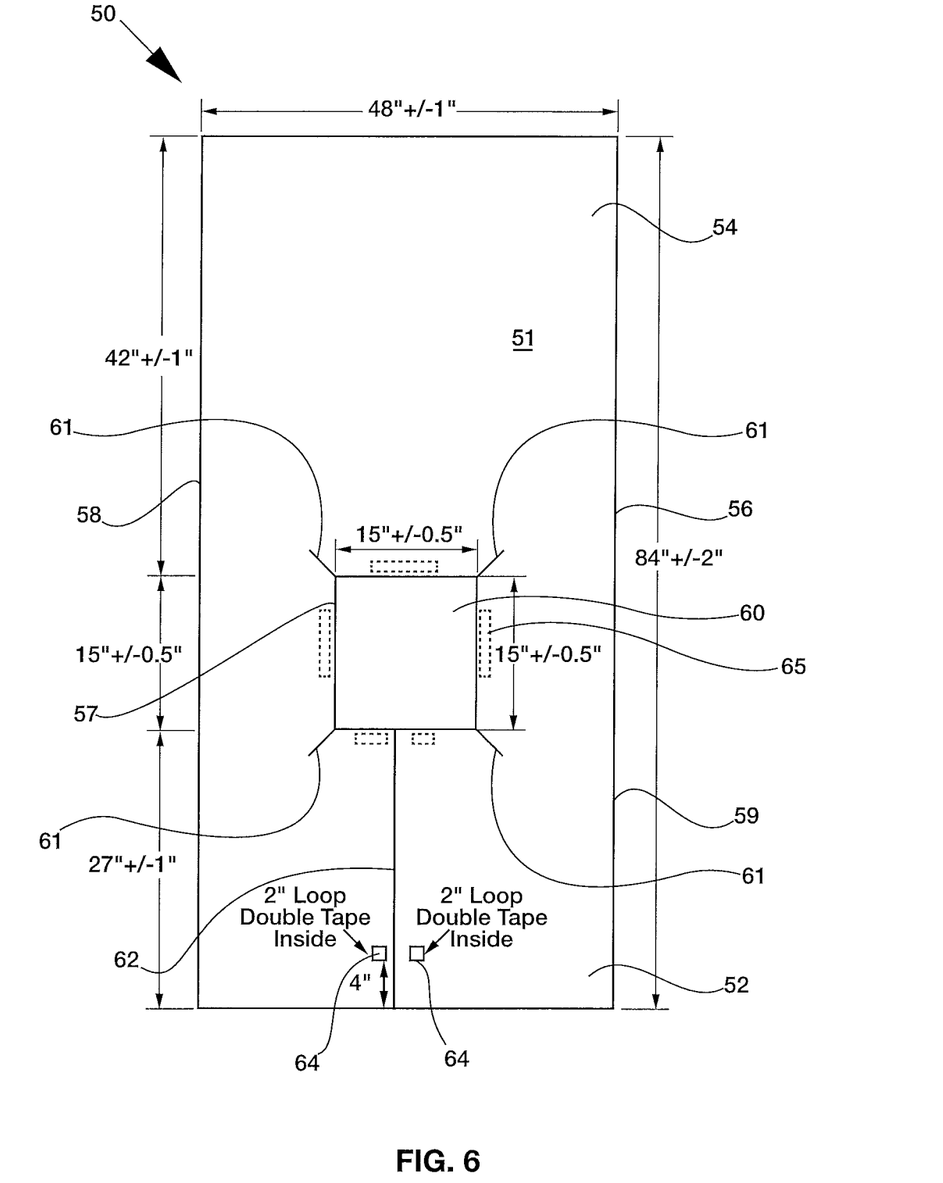
FIG. 6 is a top planar view of another example of a table base drape according to the present disclosure.

In some embodiments, the drape may be a table base drape. FIGS. 4-6 are top views of examples of a table base drape 50 according to the present disclosure. A table base drape may include a top surface 51; a bottom surface 53; a first end 52; a second end 54 and may be configured to form a perimeter around a table base. The table base drape 50 may have a long end 54 and a shorter end 52. In some examples, a table base drape 50 includes an opening 60 in the drape for fitting the table base drape around a table base. In other examples, the opening 60 may be a keyhole opening with a discontinuous section 62 of the table base drape 50, for example a slit from an outer perimeter 59 of the drape to an inner perimeter of the drape 57. The discontinuous section 62 may be formed by two adjoining sides. The adjoining sides may overlap. The adjoining sides may extend substantially in a transverse direction from the ends 52, 54 and/or the sides 56, 58 between the outside perimeter 59 and the inside perimeter 57. There may be more than one discontinuous section 62 in table base drape 50. The discontinuous section may be secured by attachment points 64.

The inner perimeter 57 of the table base drape may surround or be fitted to a table base. The inner perimeter 57 may take on any shape, by way of example, square, rectangular, rounded, etc. There may be at least one slit 61 along the inner perimeter 57 of table base drape 50 in order to fit more securely with the table base. The table base drape 50 may have an outer perimeter 59 that extends beyond an outer perimeter of the medical table. There may be adhesive strips 65 located about the inner perimeter 57 that secure the inner perimeter around the table base. Adhesive strips 65 may take on any shape and be located at any position about the inner perimeter 57.

In some embodiments, a drape 10 and a table base drape 50, as described above, may form a drape system for containment of medical waste fluids. In particular examples, the drape 10 may have attachment points that interface with attachment points on the table base drape 50 so the drapes form an attached drape system. A drape 10 and table base drape 50, two-piece drape system, creates in some examples, a maximum amount of table coverage and absorbency of the drape system, without encumbering the function of the table and/or the surgical personnel at work. The drape system 10, 50 creates an adjustable drape system for use with different sizes of medical table. Floor mats may also be used in conjunction with a table base drape and/or a drape system.

In some examples, drape 10 and/or drape 50 may be formed of layers. An impervious layer may form all or a portion of the bottom surface 23, 53 as a backing with an absorbent material layer forming all or a portion of the top surface 21, 51. In embodiments with a bottom imperious layer and an absorbent top layer, it is desirable for the drape to be flexible enough to allow for attachment of other technical or mechanical fixtures, such as for example, surgical rail clamps and/or arm boards. In some examples, such fixtures attach over the drape so an opening in the drape does not allow waste fluid to migrate through the opening to contaminate the underside and the table.

In some examples, the layers of the drapes 10, 50 may include a polyethylene layer, at least one layer of wood paper, a layer of polypropylene non-woven and a glue, such as a hot melt glue. In other examples, the layers of the drapes 10, 50 may include a layer of polyethylene, a layer of non-dust air laid paper, a layer of thermal bonding non-woven polypropylene and an adhesive. Plastics, non-wovens and combinations for use in the drapes are also considered within the scope of this disclosure.

Superabsorbent polymer may be included in the drape 10, 50. In some examples, superabsorbent polymer may extend along the central portion of drape 10, in some instances, from a substantial part of the central portion from end to end, for example from where the central portion joins the first end cover 30 to where the central portion joins the second end cover 30'. In other embodiments, the superabsorbent polymer may extend along the side portions 22, 22'. In still other examples, superabsorbent polymer may be included in the trough 41. Superabsorbent polymer may be in greater amounts in parts of the drape 10 and/or 50. The superabsorbent polymer areas included in the drape 10, 50 are configured so that, in certain embodiments, the fluids are absorbed by the drapes so as not to cause unabsorbed pooling of fluids that may readily spill if the drape is dislodged. By way of example, fluids directed toward the trough may be absorbed along the way to the trough and/or after reaching the trough.

The table base drape 50 may be, in some examples from about 77" to about 92" in length and from about 40 to about 56" in width. The drape 10 may be, in some examples from about 22" to about 30" wide at the central portion 20, from about 34" to about 50" wide on the side portions 22, 22', and from about 76" to about 92" in length at the central portion 20 and/or the side portions 22, 22'. Lengths and widths are exemplary and other dimensions are considered within the scope of this disclosure.

Attachment points 32, 64 may be any attachment securing structures, for example, hook and eye closures, buttons, fixed stitching, gluing, glue dots, strip adhesives, Velcro, buttons, binders, clips, clamps, drawstrings, and or hook and loop. More than one attachment point along the trough may increase surface area contact of the absorbent top surface with the waste fluids and may increase absorbent uptake of the waste fluids. Attachment points may take on any various shape, for example, strip adhesives may be square, circular, rectangular, linear, etc.

Figure 7A:
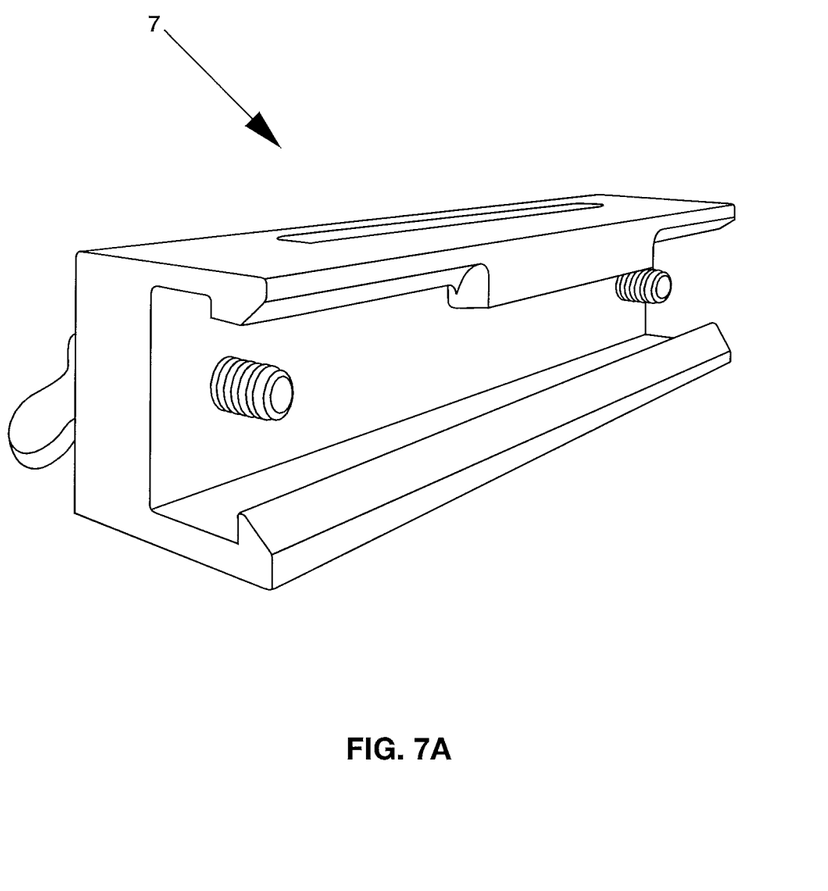
FIG. 7A is a bottom perspective view of one example of an over drape clamp according to the present disclosure.
Figure 7B:
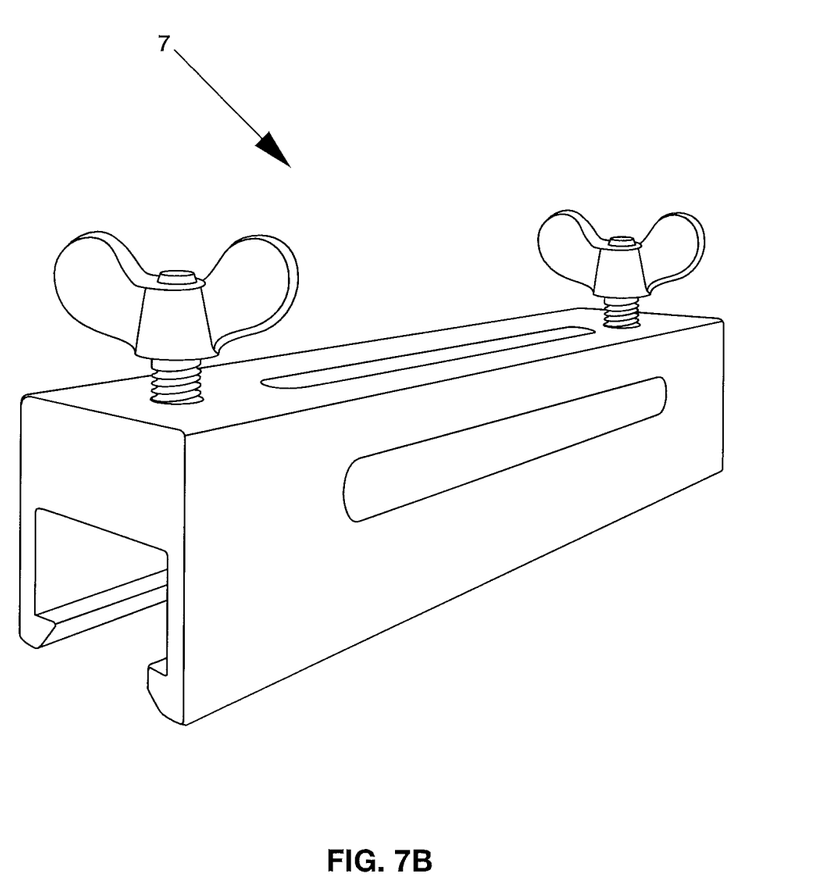
FIG. 7B is a side perspective view of one example an over drape clamp according to FIG. 7A.

In some examples, over drape clamps 70 may be included to assist in securing attachment mechanisms to the table. Conventionally, clamps attach directly to side rails of the medical and operating room tables, however, in this scenario attaching to the side rails could cause perforations in the impervious drape and/or require an opening in the drape or create an exposed area of the table, preventing the drape from forming an impervious barrier. FIGS. 7A and 7B show examples of over drape clams.

The over drape clamp 70, may attach either front to back or top to bottom over the drape. The clamp creates an attachment point for patient securement straps while not compromising the integrity of the impervious barrier provided by the drape. Clamps include a smooth gripping surface that resists ripping or tearing the more sensitive absorbent surface of the drape.

Figure 8A:
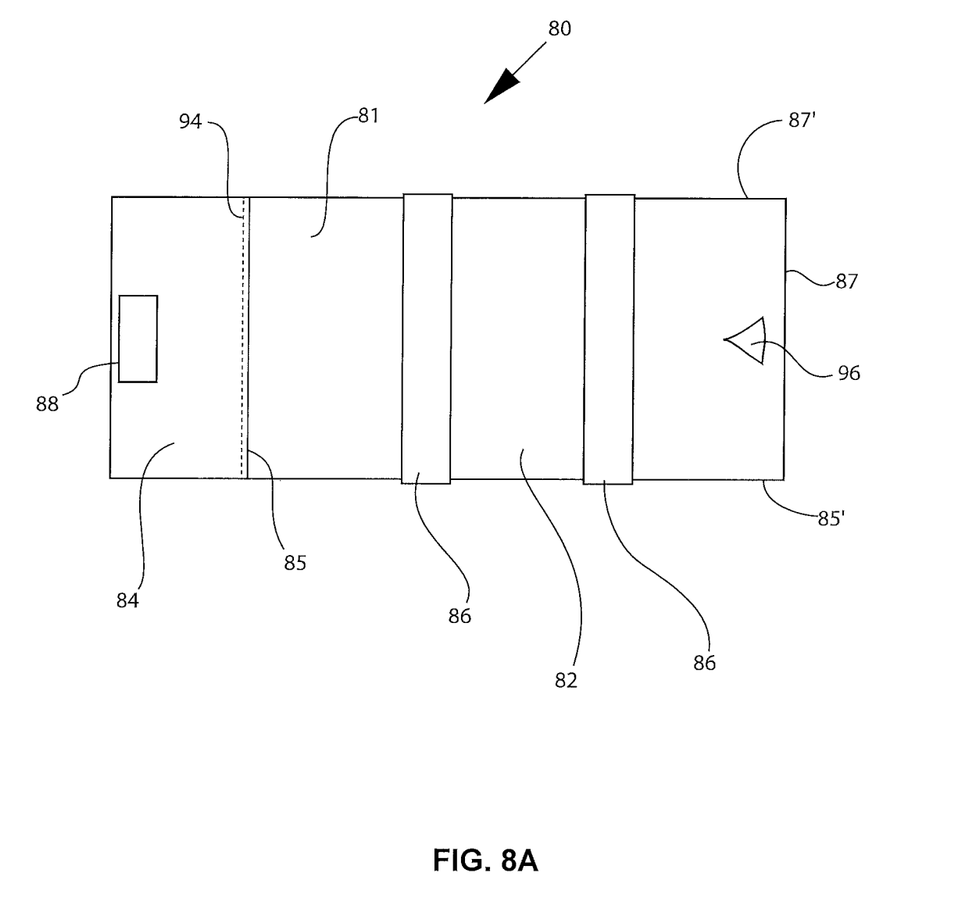
FIG. 8A is a bottom view of an example of a drape extension cover showing a flap in extension.
Figure 8B:
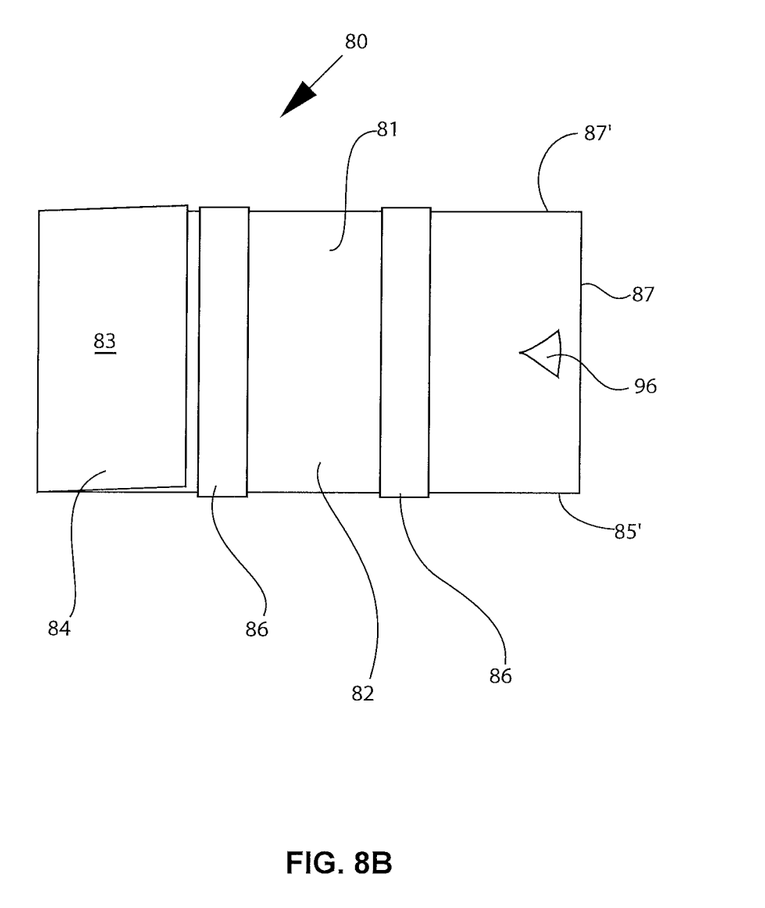
FIG. 8B is a bottom view of an example of a drape extension cover showing a flap in a folded position.
Figure 8C:
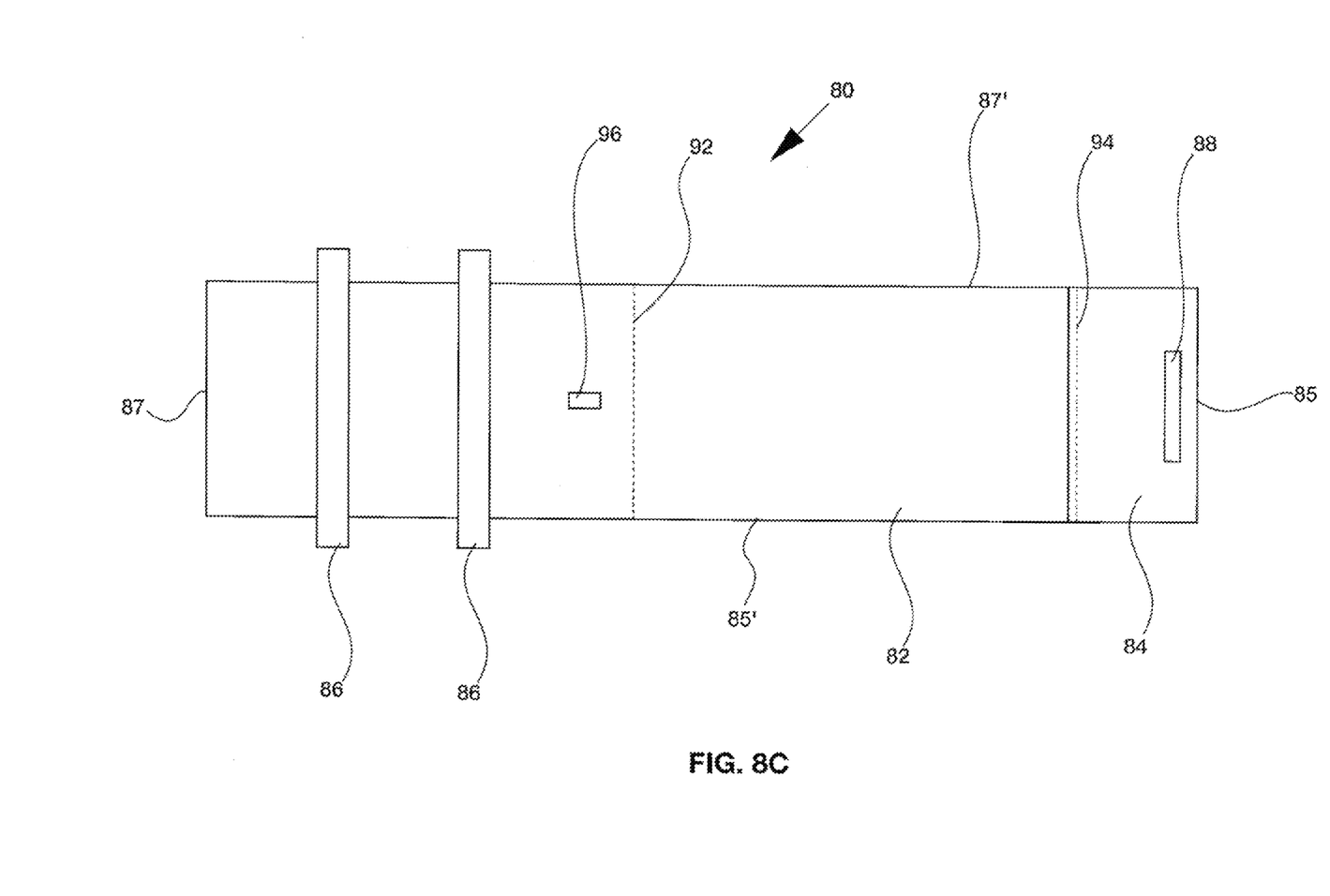
FIG. 8C is a bottom view of another example of a drape extension cover.
Figure 9:
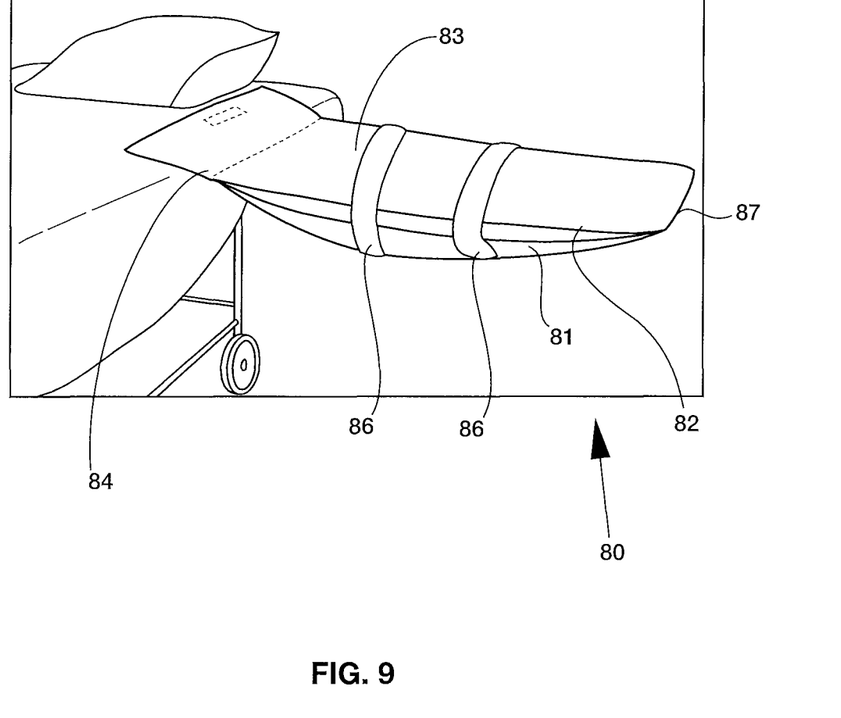
FIG. 9 shows one example of a drape system including a drape extension cover according to an embodiment of the present disclosure.

In some embodiments, reference FIGS. 8A-8C, one example of the invention may include a drape extension cover 80. Drape extension cover 80 may be any peripheral drape covers that protect accessory medical table parts beyond the main body of the table, for example, that are extensions of the main table. In one example, an accessory part may be considered an arm extension and, in other examples, may include a face cushion and/or a medical device surface.

Drape extension covers 80 may include a cover body 82, a top surface 83, a bottom surface 81 and a flap 84. The drape extension cover 80 may also include a first end 85 and a second end 87, a first side 85' and a second side 87'. The second end 87 may be a terminating end and the first end 85 may be a non-terminating end, with a flap 84 extending beyond the first end 85. The sides 85', 87' may be substantially parallel from the first end 85, extending to the second end 87.

The flap 84 may extend from only one of the surfaces, by way of example, flap 84 may extend from the top surface 83 beyond first end 85. Flap 84 may fold at a fold line 94 near first end 85 onto and overlapping with the bottom surface 81. Flap 84 may also extend substantially linearly from top surface 83, beyond first end 85. Flap 84 may include an attachment 88 for securing the flap 84 to another drape, for example, a drape 10. Drape 10 may also include an attachment that mates with the attachment 88 on the flap 84. The attachment 88 may, by way of example, be an adhesive strip, a button, a Velcro attachment, a hook and/or a snap. The flap 84 may be configured to extend across a gap between a medical table/drape covering a medical table and/or accessory medical table parts to protect side connections and in the gaps between side connections and the medical table from contamination that may access the medical table through one of the gaps.

Drape extension cover 80 may also include a closed end and an open end. Drape extension cover 80 may include straps 86 for tightening the cover 80 around an item. Drape extension cover 80 may include more than one strap 86. Drape extension cover 80 may include an access slot 96. Access slot 96 may take on any shape and may provide an opening in one of the surfaces 81, 83.

The drape extension cover 80 may be made similarly to any of the drapes disclosed herein. In one example, the drape 80 may be an impervious, absorbent, non-woven configuration. Some embodiments may include a drape cover blank with the entire drape body in extension in the blank form and extending in a single plane. The blank may be folded along a fold line 92, typically offset from the median line along the longest length of the blank. This folding, folds the blank in half lengthwise along the length of the blank to the fold line 94, leaving the fold 84 extended beyond the overlapping surfaces. The folded blank may be attached along the sides, 85', 87' in an impervious attachment, leaving three outside edges of the blank attached and one end 85 open, forming an enclosure within the drape extension cover 80 having an extending flap 84 for fluid control in medical scenarios. The impervious attachment may, for example, be reinforced sealed seams.

A drape system as described herein, may also include one or more drape extension covers 80.

A drape kit may include a drape 10, a table base drop 50 and at least one drape extension cover 80. Some kit embodiments include a drape kit 10, a table base drop 50 and two extension covers 80 specific to cover armboards to provide 360 degree protection for medical table, medical table controls and electronics and simplifies the medical room turnover process. The kit may also include a headrest cover and/or pillow cover.

Methods for protecting a medical table and/or a medical table base by any of the drapes disclosed herein are considered within the scope of this disclosure. In some examples, methods for containment of medical waste fluids by any of the drapes disclosed within are also within the scope of this disclosure. A method for protection of a medical table may include enclosing a medical table with a drape having a central portion, a first end cover and a second end cover, and a first and a second extended side portion; forming at least one trough from a folded portion and securing the trough with an attachment point. The trough may form a cuff. The drape may include preformed troughs. Methods may also include securing a drape having an inner perimeter about a table base to protect the table base from contamination from medical wastes; securing the inner perimeter about the table base; and mating a discontinuous section of the drape to create a continuous perimeter about the table base. The method may also include securing at least one extension drape cover on a table extension and extending an integral flap of the cover to protect an otherwise uncovered gap between the table and table extension. Also included may be securing the flap at an attachment point by mating an attachment point on the drape 10 and an attachment point on the flap 84.

Numerous characteristics and advantages have been set forth in the foregoing description, together with details of structure and function. Many of the novel features are pointed out in the appended claims. The disclosure, however, is illustrative only, and changes may be made in detail, especially in matters of shape, size, and arrangement of parts, within the principle of the disclosure, to the full extent indicated by the broad general meaning of the terms in which the general claims are expressed. Directional terms such as, "upward," "downward," "right" and "left," are used for convenience and not intended to limit the disclosure. It is further noted that, as used in this application, the singular forms "a," "an," and "the" include plural referents unless expressly and unequivocally limited to one referent.

I claim:

1. A drape extension cover for containment of medical waste fluids, said drape extension cover comprising:
   a top surface;
   a bottom surface;
   a first end;
   a second end;

wherein said drape extension cover is configured to form a perimeter around a medical table extension;

the drape extension cover including layers, the layers including an impervious bottom layer and an exposed absorbent top layer;

an opening in said drape extension cover for fitting said drape extension cover around a table extension, and a flap section extending from a body of said drape extension cover;

wherein said flap section extends to cover a discontinuous section between a medical table and a medical table extension and forms a continuous drape perimeter around the medical table and the medical table extension.

2. The drape extension cover of claim 1 wherein said cover is formed from a drape blank, said blank extended in a singular plane.

3. The drape extension cover of claim 2 wherein said cover is doubled upon itself along the length of the blank along a fold line that is offset from the median between a first end and a second end of the blank.

4. The drape extension cover of claim 3 wherein an inner enclosure of said cover secures around the medical table extension.

5. The drape extension cover of claim 4 including a flap that extends from one of the surfaces, beyond the first end.

6. The drape extension cover of claim 5 wherein said flap and a drape covering the medical table are secured to one another by attachment points.

7. The drape extension cover of claim 6 including at least one strap securing said drape extension cover to said medical table extension.

8. The drape extension cover of claim 7 including an adhesive strip for securing said flap to said medical table.

9. The drape extension cover of claim 8 wherein the absorbent layer includes a super absorbent polymer.

* * * * *